United States Patent [19]

Dussourd d'Hinterland et al.

[11] Patent Number: 4,933,440

[45] Date of Patent: Jun. 12, 1990

[54] **IMMUNOMODULATORS OBTAINED SEMISYNTHETICALLY FROM A BACTERIAL POLYSACCHARIDE ISOLATED FROM A NON-ENCAPSULATED MUTANT STRAIN OF *KLEBSIELLA PNEUMONIAE***

[75] Inventors: Lucien Dussourd d'Hinterland; Gérard Normier; Anne-Marie Pinel, all of Castres, France

[73] Assignee: Pierre Fabre Medicament, Paris, France

[21] Appl. No.: 50,248

[22] Filed: May 12, 1987

[30] Foreign Application Priority Data

May 12, 1986 [FR] France .................................. 86 06765

[51] Int. Cl.$^5$ .................. A61K 31/71; A61K 39/108; C07K 15/14
[52] U.S. Cl. ...................................... 536/53; 536/1.1; 514/889; 424/92
[58] Field of Search ...................... 536/1.1, 53; 424/92; 514/889

[56] References Cited

U.S. PATENT DOCUMENTS

| | | | |
|---|---|---|---|
| 4,476,119 | 10/1984 | della Valle et al. ................. | 514/25 |
| 4,501,693 | 2/1985 | Dussourd d'Hinterland et al. ......................................... | 435/70 |
| 4,593,091 | 6/1986 | della Valle et al. ................. | 514/54 |
| 4,713,374 | 12/1987 | della Valle et al. ................. | 536/53 |
| 4,716,223 | 12/1987 | della Valle et al. ................. | 536/53 |
| 4,734,403 | 3/1988 | Dussourd d'Hinterland et al. ......................................... | 536/1.1 |
| 4,755,381 | 7/1988 | Cryz ..................................... | 424/92 |
| 4,783,527 | 11/1988 | Falkowski et al. ................... | 536/53 |

FOREIGN PATENT DOCUMENTS

| 89266 | 9/1983 | European Pat. Off. . |
|---|---|---|
| 115988 | 8/1984 | European Pat. Off. . |
| 180564 | 5/1986 | European Pat. Off. . |

*Primary Examiner*—Ronald W. Griffin
*Attorney, Agent, or Firm*—Blakely, Sokoloff, Taylor & Zafman

[57] ABSTRACT

The invention relates to a polysaccharide derivative which is an amide, an ester, an ether, a salt or a quaternary ammonium derivative of D.25 with an amine, an acid or an alcohol.

15 Claims, No Drawings

IMMUNOMODULATORS OBTAINED SEMISYNTHETICALLY FROM A BACTERIAL POLYSACCHARIDE ISOLATED FROM A NON-ENCAPSULATED MUTANT STRAIN OF *KLEBSIELLA PNEUMONIAE*

The present invention relates to new immunostimulatory agents derived from the compound designated D.25.

The product designated D25 is the polysaccharide extracted from the bacterial membrane proteoglycans which is composed mainly of glactose units and has a molecular weight of 30±10 kD. This polysaccharide was described in French Patent No. 84/13,844, although the molecular weight is shown as being higher.

This polysaccharide possesses immunostimulatory properties, in particular with respect to the induction of endogenous interferon and the activation of NK cells (Natural Killers). This polysaccharide is preferably isolated from a non-encapsulated and non-pathogenic mutant strain of Klebsiella pneumoniae biotype A, deposited with the Collection Nationale de l'Institut Pasteur (National Collection of the Pasteur Institute) under No. 145-I-IP.

The present invention relates to semisynthetic derivatives of this compound D.25, and more especially to compounds of the amide, ester, or ether type of D.25, as well as the salts and quaternary ammonium derivatives.

Among these compounds, there should be mentioned the derivatives of D.25 with acids, amines or alcohols having a fatty chain, that is to say possessing at least 4 alicyclic carbon atoms.

This type of compound having a lipophilic chain modifies the hydrophilic nature of D.25 and hence its affinity and the interactions with cell membranes.

The grafting of a hydrophobic portion onto this molecule enables its capacity for interaction with the membrane of immunocompetent cells, and hence its immunostimulatory and adjuvant properties, to be increased and/or modulated.

Thus, in the case of allergens such as, for example, those of pollen, of hymenoptera venom or of acarids, or ovalbumin, which may advantageously be coupled with D.25, the immune properties of the conjugates obtained are different from those of the initial allergens. It is thus possible to orientate the immune response towards protection, with the appearance of IgG, instead of the allergic response associated with the appearance of IgE.

Naturally, the chains can contain other groups or hetero atoms, according to the nature of the compound desired.

On the other hand, among the drivatives of D.25, there should be mentioned the conjugates of D.25 with a drug having a pharmacological activity; in this case, the drug is bound to the D.25 via a bifunctional arm containing an acid, amine or alcohol group, as stated above, and another group depending on the drug to be conjugated.

Among the compounds in question, there may be mentioned the derivatives of formulae:

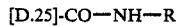  (I)

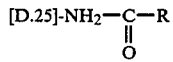  (II)

[D.25]-O—R    (III)

in which R is an aliphatic or acyl radical for (I) and (III) and an amino radical for (II) which can be substituted.

Among aliphatic radicals, there should be mentioned linear or branched alkyl radicals preferably having from 1 to 30 carbon atoms, preferably from 4 to 16 carbon atoms, as well as alkenyl and alkynyl radicals having from 2 to 30 carbon atoms and preferably from 4 to 16 carbon atoms.

Among acyl radicals, the radicals corresponding to the above aliphatic radicals are preferred.

Among amino radicals, there should be mentioned the amino radicals also corresponding to the above aliphatic radicals.

The acyl or amino radicals can also correspond to peptides or natural or synthetic proteins.

Among the substituents of R, there may be mentioned primary, secondary or tertiary amino radicals, carboxyl and acyloxy radicals and aliphatic-O- and hydroxyl radicals.

The radicals which are substituents of R are preferably secondary or tertiary amino radicals, the substituents being aliphatic radicals which can be substituted as defined above, for example:

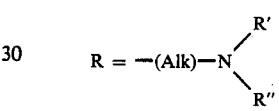

Alk is a $C_4$ to $C_{10}$ alkylene radical,
R' and R" are H, $C_1$ to $C_{16}$ alkyl or hydroxyethyl,
as well as the corresponding acyl radicals.

As above, the substituents of R can be the acyl or amino radicals corresponding to peptides or natural or synthetic proteins.

Among the compounds in question, there should be mentioned those in which R contains as substituent a drug having an activity of the same type as the D.25 activity, or an associated activity, for example retinoic acid.

"Associated activity" is understood to denote either an activity complementary to that of D.25 or an activity which boosts the D.25 activity. Finally, the compounds in question can be designed to act as carriers for D.25 or alternatively, on the other hand, be designed so that D.25 acts as carrier for them.

In the case where R contains a peptide or a protein, this is preferably a peptide or a protein which itself possesses antigenic, immunogenic and/or allergenic activity, for example one whose properties are modulated or modified by conjugation with D.25.

The compounds according to the present invention are more especially immunomodulators and adjuvants designed for use as medicinal products in the following therapeutic applications:

immunostimulants of the non-specific immune defences,
adjuvants for microbial or viral vaccines,
anticancer drugs,
inducers of endogenous interferon,
activators of the NK system and cytotoxic lymphocytes,
carrier to which allergens such as ovalbumine and allergens of acarids, hymenoptera or pollen, etc., may be coupled.

The compounds according to the invention can be obtained by known processes.

In particular, it is possible to couple the [D.25] and the derived fraction such as R-X by the coupling processes employed in peptide synthesis where the X is an amine or acid group.

Thus, it is possible to react the compound D.25 with the compound R-X in the presence of a coupling agent such as a carboniimide after, if necessary, activating one or more functional groups and protecting other functional groups, as is known in this type of synthesis.

It is also possible to employ known coupling techniques such as coupling with glutaraldehyde.

To obtain ethers, it may be necessary to activate hydroxyl groups; this is a known technique in sugar synthesis.

The invention also relates to the use of these new derivatives by way of immunostimulatory, immunomodulatory and adjuvant agents.

In particular, the invention relates to pharmaceutical compositions containing at least one such agent, and preferably an immunogenic compound or a cytotoxic product.

The examples below are designed to demonstrate other characteristics and advantages of the present invention.

EXAMPLE 1

PROCESS FOR MANUFACTURING D.25

(1) Isolation of the crude membrane proteoglycan (1.1) The biomass of Klebsiella pneumoniae strain 145-I-IP is dispersed in ice-cold Tris-HCL buffer (10 mM) pH 7.0 containing NaCl (0.15M), and then subjected to mechanical grinding designed to break the cell walls.

(1.2) The bacterial lysate is clarified by continuous centrifugation at 15,000 g and the supernatant collected.

(1.3) The supernatant is treated by adding trichloroacetic acid, qs 5% (W/V), in the cold to remove the inpurities (nucleic acids and proteins) by precipitation.

(1.4) The precipitate is removed by continuous centrifugation at 15,000 g. The clear supernatant is collected and then neutralized with NaOH.

(1.5) The solution is then dialyzed, and then concentrated by continuous ultrafiltration on Millipore membranes cutting off at 10,000 daltons.

*The concentrated solution obtained at this stage corresponds to the crude membrane proteoglycan.

(2) Isolation of the crude polysaccharide fraction (2.1) Controlled alkaline hydrolysis of the membrane proteoglycan: this operation is designed to depolymerize the crude membrane proteoglycan to liberate the polysaccharide fraction, under the following conditions:

The concentrated solution of crude membrane proteoglycan obtained above is treated with concentrated NaOH to have a final NaOH concentration of 0.5M. Hydrolysis is then carried out for 1 hour at 56° C. After rapid cooling, the solution is neutralized with HCL.

(2.2) The neutralized solution is clarified by filtration on a filter press then concentrated by ultrafiltration on a Millipore membrane cutting off at 10,000 daltons.

*The concentrated solution obtained at this stage corresponds to the crude polysaccharide fraction.

(3) Purification of the polysaccharide fraction (3.1) The concentrate obtained in paragraph 2.2 is subjected to a first chromatography on a column cast with Sephacryl S 1,000 (Pharmacia) in Tris-HCL buffer (10 mM) pH 7, which enables the high molecular weight contaminants present in the exclusion peak to be removed.

(3.2) The elution peak of the column containing the polysaccharide fraction is still slightly contaminated with proteins of very similar molecular weight (70,000 to 100,000). These proteins are hydrolyzed for 2 hours at 37° C. by the action of proteinase K at 50 μg/ml in Tris-HCL buffer (10 mM) pH 7 containing EDTA (1 mM).

(3.3) The contaminant proteins whose molecular weight has been reduced by proteolysis are separated from the polysaccharide fraction by chromatography on a column of Sephacryl S 200 (Pharmacia) in distilled water.

(3.4) The elution peak containing the purified polysaccharide fraction is collected and then concentrated by ultrafiltration on a Millipore membrane cutting off at 10,000 daltons.

(4) Production of D.25 from the polysaccharide fraction

The polysaccharide fraction obtained in paragraph 3.4 contains a few fatty acid molecules which are removed after controlled acid hydrolysis to liberate coupling sites for the purpose of preparing the semisynthetic derivatives of D.25.

(4.1) The concentrated solution obtained in paragraph 3.4 is treated with concentrated acetic acid in the proportion of 1% (v/v) and then heated to 90° C. for 90 minutes.

(4.2) After rapid cooling, the lipid substances dissociated from the D.25 precipitate and are separated by centrifugation.

(4.3) The supernatant thereby obtained is neutralized with dilute NaOH and then dialyzed and concentrated by ultrafiltration on a Millipore membrane cutting off at 10,000 daltons.

(4.4) The concentrated solution is filtered on a 0.2 μm membrane and the filtrate is then lyophilized.

*This lyophilisate corresponds to the D.25 which forms the subject of the present invention, and from which the semisynthetic derivatives will be produced. Its molecular weight is then in the region of 30±10 kD.

EXAMPLE 2

STRUCTURE OF D.25

The structure of D.25 contains on the one hand a linear polysaccharide chain consisting of an approximately 5-fold repetition of a monomeric unit of 10 sugars, and on the other hand a single, more complex linkage sequence to which short peptide chains are linked.

The repeated monomeric unit of the linear polysaccharide chain contains only galactose in pyran and furan form in the following proportions: 3 β Gal p, 3 α Gal p, 2 β Gal f, 2 α Gal f.

The sequence of this monomeric unit is as follows:

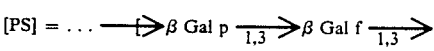

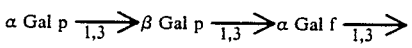

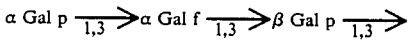

-continued

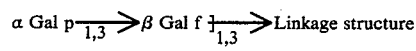

The single linkage structure is bound to the end of the linear polysaccharide chain. It contains glucose, galactose, glucosamine, heptose and mannodeoxyoctulosonic acid residues. Short peptide chains are linked to this structure.

The probable sequence is as follows:

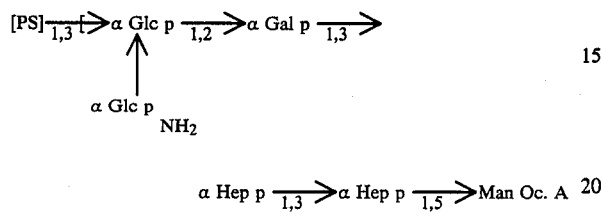

The associated peptide chains are composed of the following amino acids:
aspartic acid (3)
glutamic acid (2)
serine (1)
proline (1)
glycine (1.5)
alanine (2)
valine (1)
leucine (1)
lysine (1)

Abbreviations:

| | |
|---|---|
| β Gal p | = β Galactopyranose |
| α Gal p | = α Galactopyranose |
| β Gal f | = β Galactofuranose |
| α Gal f | = α Galactofuranose |
| α Glc p | = α Glucopyranose |
| α Glc p, NH$_2$ | = α Glucosamine |
| α Hep p | = α Heptose (D-mannoheptose) |
| Man Oc. A | = 3-deoxy-mannooctulosonic acid |

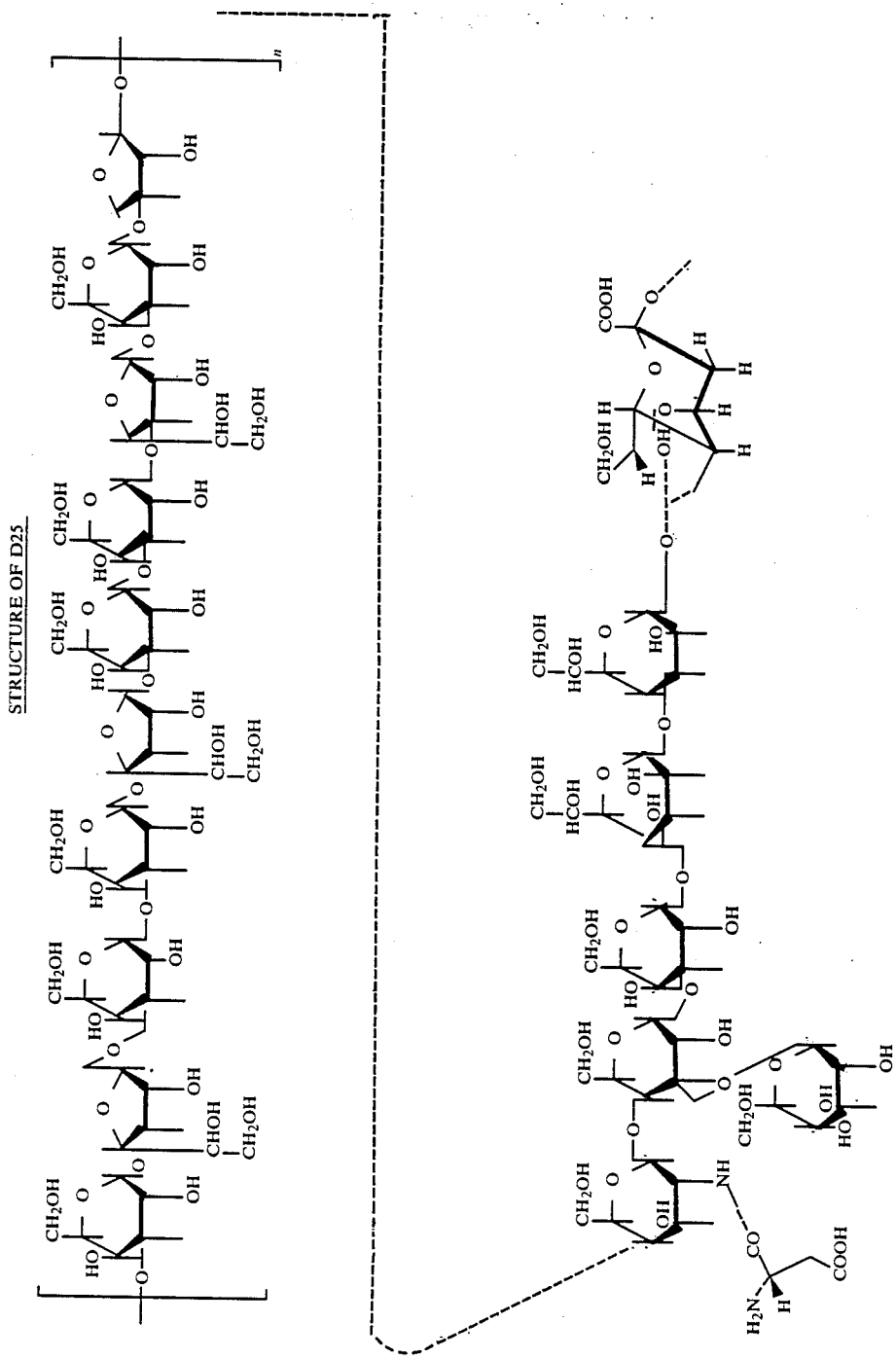

EXAMPLE 3

COUPLING OF N-BUTYRAMIDE TO D.25

(N-Butyramide = $CH_3-CH_2-CH_2-CONH_2$; MW = 87.12)

(a) 100 mg of D.25 are dissolved in 5 ml of distilled water and the pH of the solution is adjusted to pH 4.5 with dilute HCl.

(b) 3 mg of N-butyramide are dissolved in 1 ml of distilled water. 1 ml of an aqueous solution containing 6 mg/ml of EDCI [1-ethyl-3-(3-dimethylaminopropyl)-carbodiimide hydrochloride] is added to this solution. The pH is adjusted to pH 4.5 and the mixture is then stirred for 1 hour at room temperature.

The two solutions (a) and (b) are mixed and then stirred overnight at room temperature.

The D.25-butyramide complex thereby formed is then freed from excess reagents by chromatography on a 2×60 cm column of Sephadex G-25 (Pharmacia) in distilled water.

The exclusion peak containing the D.25-butyramide complex is collected and then lyophilized.

EXAMPLE 4

COUPLING OF OCTYLAMINE TO D.25

(Octylamine = $CH_3(CH_2)_6-CONH_2$; MW = 129.2)

(a) 100 mg of D.25 are dissolved in 5 ml with distilled water and the pH of the solution is adjusted to pH 4.5 with dilute HCl.

(b) 5 mg of octylamine are dissolved in 4 ml of ethyl alcohol, and 1 ml of an aqueous solution containing 20 mg of CMCI [1-cyclohexyl-3-(2-morpholinoethyl)-carbodiimide] is added to this solution. The pH is adjusted to 4.5 and the mixture is then stirred for 1 hour at room temperature.

To two solutions (a) and (b) are mixed and then stirred overnight at room temperature.

The excess reagents are then separated from the complex by chromatography on a column of Sephadex LH-20 (Pharmacia) equilibrated beforehand with 50% strength ethanol.

The peak containing the complex is collected at the exclusion volume and the complex is precipitated by adding 4 volumes of acetone. The precipitate is collected by filtration, washed with acetone and then dried under vacuum over $P_2O_5$.

EXAMPLE 5

COUPLING OF DODECANOIC ACID TO D.25

(Dodecanoic acid = $CH_3(CH_2)_{10}-COOH$; MW = 200.32)

(a) 100 mg of D.25 are dissolved in 5 ml of distilled water.

(b) 5 mg of dodecanoic acid are dissolved in 5 ml of THF (tetrahydrofuran) and 6 mg of EEDQ (N-ethoxycarbonyl-2-ethoxy-1,2-dihydroquinoline) are then added to this solution. The mixture is stirred for 1 hour at room temperature.

The two solutions (a) and (b) are mixed and stirred overnight at room temperature.

The excess unbound fatty acid is then removed by means of several extractions with chloroform, and the D.25-dodecanoic acid complex is dialyzed against distilled water and then lyophilized.

EXAMPLE 6

COUPLING OF A DIAMINO-SPACER TO D.25 TO PERMIT THE SUBSEQUENT COUPLING OF SUBSTANCES HAVING A FREE CARBOXYL (Example: coupling 1,4-diaminobutane-D.25 = D.25-DAMB)

50 mg of D.25 and 300 mg of diaminobutane in 50 ml of potassium phosphate buffer (0.1M) pH 6.1 are treated with 300 mg of EDCI [1-ethyl-3-(3-dimethylaminopropyl)carbodiimide, HCl]. After two hours' stirring at room temperature, the mixture is dialyzed against $NaHCO_3$ buffer (0.05M) pH 8.3 at 4° C., changed several times to remove the excess reagents.

The dialysate is lyophilized = D.25-DAMB.

EXAMPLE 7

COUPLING OF A POLYLYSINE TO THE D.25-DAMB OBTAINED IN EXAMPLE 6

50 mg of D.25-DAMB and 60 mg of polylysine of MW 5,000–10,000 in 5 ml of distilled water are treated with 20 mg of cyanamide (Sigma). After being stirred overnight at room temperature, the mixture is dialyzed against distilled water and the peak containing the complex (one elution peak) is collected and then lyophilized: D.25-polylysine.

EXAMPLE 8

PRODUCTION OF A D.25-DAMB-RETINOIC ACID DERIVATIVE 25 mg of D.25-DAMB and 5 mg of retinoic acid are dissolved in 3 ml of tetrahydrofuran. 18 mg of DCCI (dicyclohexylcarbodiimide) are added to this solution and the mixture is then left with stirring for 18 hours at room temperature.

3 ml of distilled water are then added and a series of extractions with chloroform are then performed to extract the excess reagents. The D.25-retinoic acid derivative present in the aqueous phase is dialyzed against distilled water and then lyophilized.

EXAMPLE 9

COUPLING OF OVALBUMIN (ova) TO D.25

100 mg of D.25 and 100 mg of ova are dissolved in 10 ml of distilled water. The pH of the solution is brought to 4.7 with 0.1N HCl. 1 ml of a solution containing 0.5 mg of CMCI [1-cyclohexyl-3-(2-morpholinoethyl)carbodiimide] is then added to this solution. The mixture is then stirred for 1 hour at room temperature while the pH is maintained at 4.7, and then overnight at +10° C.

The D.25-ova conjugate is purified by chromatography on a column of Sephacryl S-200 (Pharmacia) in 0.1M phosphate buffer pH 7.4. The peak containing the D.25-ova conjugate (first elution peak) is collected, dialyzed and then lyophilized.

The conjugate thereby obtained contains 1 molecule of ovalbumin per molecule of D.25.

We claim:

1. A polysaccharide derivative which is an amide, an ester, an ether, a salt or a quaternary ammonium derivative of D.25 with an amine, an amide, and acid or an alcohol.

2. The derivative as claimed in claim 1, wherein the derivative is obtained with a fatty amine, acid or alcohol.

3. The derivative as claimed in claim 1, wherein the amine, acid or alcohol contains at least 4 alicyclic carbon atoms.

4. The derivative as claimed in claim 1, wherein the amine, acid or alcohol is coupled with a drug having a pharmacological activity.

5. The derivative as claimed in claim 1, which possesses the formula selected from:

{D.25}—CONH—R   (I)

{D.25}—NH—CO—R   (II)

{D.25}—O—R   (III)

in which R is an aliphatic or acyl radical for (I) and (III) and amino radical for (II), and wherein R is substituted or non-substituted.

6. The derivative as claimed in claim 5, wherein R is substituted by primary, secondary or tertiary amino radicals, carboxyl, acyloxy or alcoxycarbonyl radicals and hydroxyl and aliphatic-oxy radicals.

7. The derivative as claimed in one of claims 5 or 6, wherein the radical R contains from 1 to 30 alicyclic carbon atoms.

8. The derivative as claimed in claim 5, wherein the radical R contains from 4 to 16 alicyclic carbon atoms.

9. The derivative as claimed in claim 5, wherein R is the radical derived from a peptide or a portein.

10. The derivative as claimed in claim 5, wherein the substitutent of R is the radical derived from a peptide or a protein.

11. The derivative as claimed in claim 5, wherein:

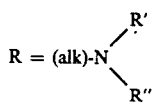

alk is a $C_4$ to $C_{10}$ alkylene radical, and R' and R" are, independently, H, $C_1$ to $C_{10}$ alkyl or hydroxyethyl, or a drug.

12. The derivative as claimed in claim 5, which possesses the formula selected from:

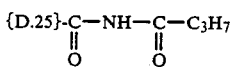

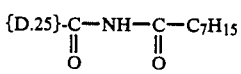

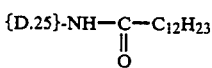

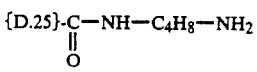

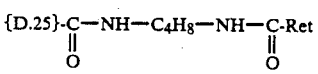

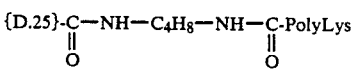

{D.25}-allergen

Ret being a retinoic acid radical,
Polylys being a polylysine radical.

13. An immunostimulatory agent as claimed in one of claims 1 to 6 or 8 to 12.

14. A therapeutic composition containing at least one derivative as claimed in one of claims 1 to 6 or 8 to 12.

15. The composition as claimed in one of claims 1 to 6 or 8 to 12, containing in addition an immunogenic compound or a cytotoxic product.

* * * * *